United States Patent [19]
Carver et al.

[11] Patent Number: 5,962,467
[45] Date of Patent: *Oct. 5, 1999

[54] DERIVATIVES OF SWAINSONINE AND THEIR USE AS THERAPEUTIC AGENTS

[75] Inventors: Jeremy Carver; Rajan Shah, both of Toronto, Canada

[73] Assignee: GlycoDesign, Inc., Toronto, Canada

[ * ] Notice: This patent is subject to a terminal disclaimer.

[21] Appl. No.: 08/897,656

[22] Filed: Jul. 21, 1997

Related U.S. Application Data

[63] Continuation of application No. 08/474,077, Jun. 7, 1995, Pat. No. 5,650,413.

[51] Int. Cl.[6] ........................ A61K 31/435; C07D 471/04

[52] U.S. Cl. ........................ 514/299; 546/112; 546/183

[58] Field of Search ........................ 546/183, 112; 514/299

[56] References Cited

U.S. PATENT DOCUMENTS

| | | | |
|---|---|---|---|
| 3,274,202 | 9/1966 | Mohrbacher | 546/183 |
| 4,792,558 | 12/1988 | Sunkara et al. | 514/299 |
| 4,837,237 | 6/1989 | Rohrschneider et al. | 514/62 |
| 4,857,315 | 8/1989 | Dennis | 424/85.2 |
| 4,894,388 | 1/1990 | Fleet | 548/556 |
| 4,996,329 | 2/1991 | Fleet et al. | 548/453 |
| 5,021,427 | 6/1991 | Elbein et al. | 514/315 |
| 5,023,340 | 6/1991 | Fleet | 548/453 |
| 5,041,555 | 8/1991 | Fleet et al. | 548/541 |
| 5,075,448 | 12/1991 | Fleet | 548/453 |
| 5,075,457 | 12/1991 | Fleet | 548/453 |
| 5,187,279 | 2/1993 | Cha et al. | 546/183 |
| 5,264,356 | 11/1993 | Rohrschneider | 435/236 |
| 5,272,070 | 12/1993 | Lehrman et al. | 435/172.1 |
| 5,288,875 | 2/1994 | Cha et al. | 548/453 |
| 5,376,675 | 12/1994 | Alphey et al. | 514/425 |
| 5,382,709 | 1/1995 | Farr et al. | 568/704 |
| 5,438,069 | 8/1995 | Farr et al. | 514/1 |
| 5,466,809 | 11/1995 | Dime | 546/183 |
| 5,484,925 | 1/1996 | Cha et al. | 546/90 |
| 5,621,106 | 4/1997 | Dime | 546/183 |
| 5,633,261 | 5/1997 | Dime | 514/299 |
| 5,650,413 | 7/1997 | Carver et al. | 546/183 |

FOREIGN PATENT DOCUMENTS

| | | |
|---|---|---|
| 2040058 | 10/1991 | Canada . |
| 1298549 | 4/1992 | Canada . |
| 0004260 | 10/1979 | European Pat. Off. . |
| 0036269 | 9/1981 | European Pat. Off. . |
| 104826 | 4/1984 | European Pat. Off. . |
| 295538 | 12/1988 | European Pat. Off. . |
| 424349 | 4/1991 | European Pat. Off. . |
| 451834 | 10/1991 | European Pat. Off. . |
| 3507019 | 8/1986 | Germany . |
| 61277685 | of 0000 | Japan . |
| 60-218389 | 4/1984 | Japan . |
| 60-166680 | 8/1985 | Japan . |
| 60-193986 | 10/1985 | Japan . |
| 61-227566 | 9/1986 | Japan . |
| WO9006311 | 6/1990 | WIPO . |
| WO93/05040 | 3/1993 | WIPO . |
| WO93/05781 | 4/1993 | WIPO . |
| WO9309117 | 5/1993 | WIPO . |
| WO9535094 | 12/1995 | WIPO . |
| WO9640683 | 12/1996 | WIPO . |

OTHER PUBLICATIONS

Dennis J. W. in “Cell Surface Carbohydrates and Cell Development”, Fukuda M.(ed)., CRC Press, Boca Raton, Ann Arbor London, 1992, Chapter 6, pp. 161–194.

Dennis J. W. et al, Science, 236:582, 1987.

VanderElst, E. and J.W. Dennis, Experimental Cell Research 192: 612–621, 1991.

J.W. Dennis, Cancer Research 46:5131, 1986.

Humphries, M.J. et al, Proc.Natl. Acad, Sci, USA, 83:1752, 1986.

Colegate S.M. et al., Aust. J. Chem. 1979, 32: 2257–64, 1979.

Molyneux R.J. an L.F. James, Science 216:190, Apr. 1982.

Schneider M.J. et al, Tetrahedron 39(1): 29, 1983.

Tulsiani D.R.P. et al, J. Biol. Chem. 257:7936, 1982.

Fernandes, B. et al, Cancer Research 51: 718, 1991.

Olden K. et al, Pharmac. Ther. 50:285, 1991.

Humphries, M.J. et al, Cancer Research 48:1410, 1988.

M. Yagita and E. Sakela, Scand. J. Immunol 31:275–282, 1990.

White, S.L. et al, Biochem Biophys. Res. Commun. 150:615–625, 1988.

Seftor, R.E.B. Melanoma Research 1:43–54, 1991.

Yagel S., et al., Intl. J. Cancer 44:685, 1989.

J.W. Dennis et al, J. National Cancer Institute 81:1028, 1989.

J.W. Dennis et al, Cancer Research 50:1867, 1990.

Humphries, M.J. and K. Olden, Pharmac. Ther. 44:85–105, 1989.

White, S.L. et al., Cancer Communications, 3(30):83, 1991.

Oredipe, O.A., et al, J. National Cancer Institute, 83:1149, 1991.

J.W. Dennis, et al, Biochemical Pharmacology 46:1459, 1993.

Aoyama, H. et al, J. Org. Chem. 57: 3037–3041, 1992.

Hibbett, E. P., and J. Sam, J. Het. Chem. 7:857,1970.

Heidt, P.C. et al, Tetrahedron Letters 31: 5441, 1990.

Reinecke, M., and L.R. Kray, J. Org. Chem. 29: 1736, 1964.

Chastanet, J. and G. Roussi, J. Org. Chem, 50:2910–2914, 1985.

Bashyal, B.P. et al, Tetrahedron Letters, 3083,1987.

Clemo, G.R. and T.P. Metcalfe, J. Chem. Soc. 1937, p. 1518.

Leonard, N.J. et al, J. Org. Chem. 22:1445, 1957.

(List continued on next page.)

*Primary Examiner*—Bernard Dentz
*Attorney, Agent, or Firm*—Merchant & Gould

[57] ABSTRACT

The invention relates to novel mannosidase inhibitors, processes for their preparation and their use as therapeutic agents. The invention also relates to pharmaceutical compositions containing the compounds and their use as therapeutics

4 Claims, 1 Drawing Sheet

OTHER PUBLICATIONS

Winkler D.A. and G. Holan, J. Med. Chem., 32: 2084, 1989.
Reinecke, M.G. and L.R. Kray, J. Org. Chem 30:3671, 1965.
Bogeso, K.P. et al, J. Med. Chem. 30:142–150, 1987.
Goss P.E. et al, Cancer Res. 54: 1450, 1994.
Hino et al, J. Antibiot. (Tokyo) 38: 926–935, 1985.
Goss, P.E. et al, Clin. Cancer Res. 3:1077,1997.
Holden R.T. and R. Raper, J. Chem. Soc. p. 2545, 1963.
Biniecki, S. et al.,Chemical Abstracts, 1984, 101, No. 90743a.
Biniecki, S. et al., Chemical Abstracts, 106, 1987, 138204h.
Boegesoe, K. P., et al., Chemical Abstracts, 106, 1987, No. 84369v.
Smith, M.B. et al., Chemical Abstracts vol. 104, 1986, No. 51007f.
Hashimoto, S. et al., Chemical Abstracts vol. 106, 1987, No. 138253y.
Miyano, Se. et al, Chemical Abstracts, vol. 98, 1983, No. 179148c.
Yoon, U.C. et al., Chemical Abstracts vol. 97, 1982, No. 38827r.
Fujiwara, et al, Chemical Abstracts vol. 117, 1992, No. 211862e.
Winterfeld, K. et al., Chemical Abstracts vol. 74, 1971, No. 3456s.
Motohiro, et al., Chemical Abstracts, vol. 101, Abstract 28283x, 1984.
Temple Jr. C. and G. Rener, J. Med. Chem 32:2089, 1989.
Nicolson, G.L. Biochem Biophys. Acta. 695:113, 1982.
Tulsiani, D.R.P. et al., Archives Biochem. Biophys. 232: 76–85, 1984.
Levine, A.S. et al., Can. Res. 39: 1645–1650, 1970.
Bowlin, T. L. et al., Cancer Research 49:4109–4113, 1989.
Tulsiani, D.R.P. and O. Touster, J. Biol. Chem., 258: 7578–7585, 1983.
S.R. Wilson and R.A. Sawicki J. Org. Chem 44:330, 1979.
Villiani et al, J. Org. Chem., 6:142, 1962.
Austin, G.N. et al, Tetrahedron, 43:3095–3108, 1987.
Skelton, B.W. and White, A.H., Aust. J. Chem. 33:435–9, 1980.
Pearson, W. H. and E.J. Hembre, J. Org. Chem. 61:5546–5556, 1996.
Rodriguez, R. and F. Bermejo, Tetrahedron Letters 37: 5581–5584, 1996.
Keck, G. E. and D.R. Romer, J. Org. Chem. 58: 6083–6089, 1993.
Kim Y.G., and J.K. Cha, Tetrahedron Letters, 30:5721–5724, 1989.
Tadano, K. et al, J. Org Chem,. 53:5209–5215, 1988.
Tadano, K., et al, Bull Chem. Soc. Jpn. 59: 3885–3892, 1986.
Tadano, K., et al, Bull. Chem. Soc. Jpn., 60: 3667–3671, 1987.
Honda, T. et al, Chem. Soc. Perkin Trans. 1, p. 2091, 1994.
Suami, T. et al, Chemistry Letters, pp. 513–516, 1984.
Hembre, E.J. and W. H. Pearson, Tetrahedron 53: 11021–11032, 1997.
Fleet, G.W.J. et al., Tetrahedron Letters 26: 3127–3130, 1985.
Fleet, G.W.J. et al, Tetrahedron 44:2649, 1988.
Demetriou M. et al, J. Cell Biol. 130:383–392, 1995.
Dennis et al., Oncogene 4:853–860, 1998.
Bennett R.B. et al, J. Org. Am. Chem. Soc. 111:2580–2582, 1989.

FIGURE 1

DERIVATIVES OF SWAINSONINE AND THEIR USE AS THERAPEUTIC AGENTS

This is a continuation of application Ser. No. 08/474,077 filed Jun. 7, 1995, now U.S. Pat. No. 5,650,413.

FIELD OF THE INVENTION

The present invention relates generally to novel derivatives of swainsonine, processes for their preparation and their use as therapeutic agents.

BACKGROUND OF THE INVENTION

Swainsonine (SW) is an indolizidine alkaloid found in Australian *Swainsona canescens* (Colegate et al., Aust J Chem 32:2257–2264, 1979), North American plants of the genera Astragalus and Oxytropis (Molyneux R J and James L F., Science 215:190–191, 1981), and also the fungus *Rhizoctonia leguminicola* (Schneider et al., Tetrahedron 39;29–31, 1983). The alkaloid is a potent inhibitor of the Golgi enzyme α-mannosidase II, an enzyme required for maturation of N-linked oligosaccharides on newly synthesized glycoproteins. SW also blocks lysosomal α-mannosidases causing the accumulation of oligomannose chains in cells exposed to the drug (Tulsiani et al., J. Biol. Chem. 257:7936–7939, 1982).

The SW block in Golgi processing prevents expression of the β1+l-6GlcNAc branched "complex-type" N-linked oligosaccharides which has been observed to increase following malignant transformation in human and rodent cells (Fernandes et al., Cancer Res. 51:718–723, 1991 and Dennis, J. W., pp. 161–194. CRC Press, Boca Raton, 1991). The branched oligosaccharides appear to play a role in cancer metastasis, as loss or truncation of the structures due to somatic mutations in metastatic tumor cell lines results in greatly reduced metastasis and slower solid tumor growth (Dennis et al., Science 236:582–585, 1987 and VanderElst I. and Dennis J. W., Exp. Cell Res. 192:612–613, 1991). Furthermore, SW-treated murine tumor cells are less metastatic in both organ-colonization and spontaneous metastasis assays in mice (Dennis J. W., Cancer Res. 46:5131–5136, 1986 and Humphries et al., Proc. Natl. Acad. Sci. USA 83:1752–1756, 1986).

SW has been shown to block tumor cell invasion through extracellular matrix in vitro (Yegel et al., Int. J. Cancer 44:685–690, 1989 and Seftor et al., Melanoma Res. 1:53–54, 1991). SW administered either orally or by mini-osmotic pumps to athymic nude mice inhibited the growth rate of human MeWo melanoma and HT29m colon carcinoma tumor xenografts in the mice (Dennis et al., J. Natl. Cancer Inst. 81:1028–1033, 1989 and Dennis et al., Cancer Res., 50:1867–1872, 1990).

The alkaloid has positive effects on cellular immunity in mice (reviewed in Humphries M. J. and Olden K., Pharmacol Ther. 44:85–105, 1989, and Olden et al., Pharmacol Ther 50:285–290, 1991)). In particular, SW has been shown to alleviate both chemically-induced and tumor-associated immune suppression (Hino et al., J. Antibiot. (Tokyo) 38:926–935, 1985), increase NK cell (Humphries et al., Cancer Res. 48:1410–1415, 1988), and LAK cell activities (Yagita M and Saksela E., Scand. J. Immunol. 31:275–282, 1990), and increase splenic and bone marrow (BM) cell proliferation (White et al., Biochem. Biophys. Res. Commun. 150;615–625, 1988; Bowlin et al. Cancer Res 49, 4109–4113, 1989, and White et al., Cancer Commun. 3:83–91, 1991). SW has also been shown to be hemorestorative in mice following treatment with both cycle-specific and nonspecific chemotherapeutic agents (Oredipe et al., J. Natl. Cancer Inst. 83:1149–1156, 1991).

Japanese Patent Application No. J61277685 describes indolizidine derivatives which are reported to be useful as immune regulators, which can be administered orally or parenterally at a dose of about 0.1–100 ml/kg a day. It is also reported that the indolizidine derivatives may be used in combination with antitumour agents, antimicrobial agents or antiinflammatories.

Carbonoyloxy substitutions at the 2 and 8 carbons of swainsonine have been reported to reduce inhibitor activity by 2–3 orders of magnitude for Jack Bean and MDAY-D2 tumor cell lysosomal mannosidases in vitro. However, 2-p-nitrobenzoyloxy, 2-octanoyloxy- and 2-butanoyloxy-derivatives of swainsonine retained full activity as inhibitors of Golgi oligosacccharide processing in viable MDAY-D2 tumor cells. Inhibition of oligosaccharide processing was reduced by the esterase inhibitor diethyl p-nitrophenyl phosphate, suggesting that while the compounds are relatively poor inhibitors of mannosidase in vitro, the compounds enter cells at a rate comparable to that of SW and are converted to SW by cellular esterases. The more lipophilic esters, 2-benzoyloxy-SW, 2-toluoyloxy-SW, 8-palmitoyloxy-SW and 8-myristinoyloxy-SW, showed $IC_{50}$ values at least 10 times higher for inhibition of Golgi oligosaccharide processing, probably due to less efficient entry of the compounds into tumor cells. The anti-metastatic activities of SW and two analogs were tested and shown to correlate with the $IC_{50}$ values for inhibition of Golgi oligosaccharide processing in cultured tumor cells. In vivo, SW and the analogs were administered intraperitoneally to mice and found to have comparable activities as stimulators of bone marrow cell proliferation. (Dennis, J. W. et al. Biochemical Pharmacology 46:1459–1466, 1993).

SUMMARY OF THE INVENTION

The present inventors have found that particular derivatives of swainsonine developed by the inventors are ideally suited for use as drugs and prodrugs having improved pharmacological properties and reduced side effects. The present inventors have also identified derivatives which do not substantially inhibit lysosomal mannosidase activity. Lysosomal mannosidase activity is an undesirable side effect of swainsonine.

The present invention therefore relates to a compound of the formula I wherein one or two of $R^1$, $R^2$, and $R^3$ are the same or different and represent hydroxyl, halo, amino, or alkoxy, and the others of $R^1$, $R^2$, and $R^3$ represent hydroxyl or hydrogen, and one of $R^4$, $R^5$, and $R^6$ represents alkyl or aryl, and the other of $R^4$, $R^5$, and $R^6$ represents hydrogen.

The present invention also provides a process for the preparation of a compound of the formula I as defined herein comprising (a) when a compound of the formula I is required wherein $R^6$ is alkyl or aryl, reacting a compound of the formula II wherein $R^{1'}$, $R^{2'}$, and $R^{3'}$ are hydroxyl and $R^{4'}$, $R^{5'}$, and $R^{6'}$ are hydrogen, which is blocked at $R^{1'}$ and $R^{2'}$, with appropriate oxidizing and Grignard reagents, deblocking $R^{1'}$ and $R^{2'}$, to produce a compound of the formula I wherein $R^6$ is alkyl or aryl, $R^1$, $R^2$, and $R^3$ are hydroxyl, and $R^4$ and $R^5$ are hydrogen; or, optionally, blocking $R^{3'}$, deblocking $R^{1'}$, and replacing the free hydroxyl at $R^{1'}$ by alkoxy, halo, or amino, and deblocking $R^{2'}$ and $R^{3'}$ to produce a compound of the formula I, wherein $R^6$ is alkyl or aryl, $R^1$ is alkoxy, halo, or amino, $R^2$ and $R^3$ are hydroxyl, and $R^4$ and $R^5$ are hydrogen; or optionally, blocking $R^{3'}$, deblocking $R^{2'}$, replacing the free hydroxyl at $R^{2'}$ by alkoxy, halo, or amino, and deblocking $R^{1'}$ and $R^{3'}$ to produce a compound of the formula I wherein $R^6$ is alkyl or aryl, $R^2$ is alkoxy, halo, or amino, $R^1$ and $R^3$ are hydroxyl, and $R^4$ and $R^5$ are hydrogen; or optionally, deblocking $R^{1'}$, replacing the free hydroxyl at $R^{1'}$ by alkoxy, halo, or amino, and deblocking $R^{3'}$ to produce a compound of the formula I wherein $R^6$ is alkyl or aryl, $R^1$ and $R^2$ are the same or different and are alkoxy, halo, or amino, $R^3$ is hydroxyl, $R^4$ and $R^5$ are hydrogen;

(b) when a compound of the formula I is required wherein $R^5$ is alkyl or aryl, reacting a compound of the formula II wherein $R^{1'}$, $R^{2'}$, and $R^{3'}$ are hydroxyl and $R^{4'}$, $R^{5'}$, and $R^{6'}$ are hydrogen, which is blocked at $R^{1'}$ and $R^{3'}$, with appropriate oxidizing and Grignard reagents, deblocking $R^{1'}$ and $R^{3'}$, to produce a compound of the formula I wherein $R^5$ is alkyl or aryl, $R^1$, $R^2$, and $R^3$ are hydroxyl, and $R^4$ and $R^6$ are hydrogen; or, optionally, blocking $R^{2'}$, deblocking $R^{1'}$, replacing the free hydroxyl at $R^{1'}$ by alkoxy, halo, or amino, and deblocking $R^{2'}$ and $R^{3'}$, to produce a compound of the formula I wherein $R^5$ is alkyl or aryl, $R^1$ is alkoxy, halo, or amino, $R^2$ and $R^3$ are hydroxyl, $R^4$ and $R^6$ are hydrogen; or, optionally, blocking $R^{2'}$, deblocking $R^{3'}$, replacing the free hydroxyl at $R^{3'}$ by alkoxy, halo, or amino, and deblocking $R^{1'}$ and $R^{2'}$, to produce a compound of the formula I wherein $R^5$ is alkyl or aryl, $R^3$ is alkoxy, halo, or amino, $R^1$ and $R^2$ are hydroxyl, $R^4$ and $R^6$ are hydrogen; or, optionally, deblocking $R^{1'}$, replacing the free hydroxyl at $R^{1'}$ by alkoxy, halo, or amino, deblocking $R^{2'}$ to produce a compound of the formula I wherein $R^5$ is alkyl or aryl, $R^1$ and $R^3$ are the same or different and are alkoxy, halo, or amino, $R^2$ is hydroxyl, and $R^4$ and $R^6$ are hydrogen; or (c) when a compound of the formula I is required wherein $R^4$ is alkyl or aryl, reacting a compound of the formula II wherein $R^{1'}$, $R^{2'}$, and $R^{3'}$ are hydroxyl and $R^{4'}$, $R^{5'}$, and $R^{6'}$ are hydrogen, which is blocked at $R^{2'}$, and $R^{3'}$, with appropriate oxidizing and Grignard reagents, deblocking $R^{2'}$ and $R^{3'}$, to produce a compound of the formula I wherein $R^4$ is alkyl or aryl, $R^1$, $R^2$, and $R^3$ are hydroxyl, and $R^5$ and $R^6$ are hydrogen; or, optionally, blocking $R^{1'}$, deblocking $R^{2'}$, replacing the free hydroxyl at $R^{2'}$ by alkoxy, halo, or amino, and deblocking $R^{1'}$ and $R^{3'}$ to produce a compound of the formula I wherein $R^4$ is alkyl or aryl, $R^2$ is alkoxy, halo, or amino, $R^1$ and $R^3$ are hydroxyl, $R^5$ and $R^6$ are hydrogen; or, optionally, blocking $R^{1'}$, deblocking $R^{3'}$, replacing the free hydroxyl at $R^{3'}$ by alkoxy, halo, or amino, and deblocking $R^{1'}$ and $R^{2'}$, to produce a compound of the formula I wherein $R^4$ is alkyl or aryl, $R^3$ is alkoxy, halo, or amino, $R^1$ and $R^2$ are hydroxyl, and $R^5$ and $R^6$ are hydrogen, or optionally, deblocking $R^{2'}$, replacing the free hydroxyl at $R^{2'}$ by alkoxy, halo, or amino, and deblocking $R^{1'}$, to produce a compound of the formula I wherein $R^4$ is alkyl or aryl, $R^2$ and $R^3$ are the same or different and are alkoxy, halo, or amino, $R^1$ is hydroxyl, $R^5$ and $R^6$ are hydrogen.

The invention also relates to a pharmaceutical formulation comprising a compound of the formula I as an active agent.

The invention further relates to a method for stimulating the immune system, treating proliferative disorders, or microbial infections in an individual comprising administering an effective amount of a compound of the formula I of the invention. The invention also relates to the use of a compound of the formula I in the preparation of a medicament for stimulating the immune system, and/or for treating proliferative disorders, and microbial infections.

The present invention also relates to the use of a compound of the formula I which is esterified at free hydroxyls as a prodrug.

These and other aspects of the present invention will become evident upon reference to the following detailed description and attached drawing. In addition, reference is made herein to various publications, which are hereby incorporated by reference in their entirety.

BRIEF DESCRIPTION OF THE DRAWINGS

The invention will be better understood with reference to the drawings in which.

DETAILED DESCRIPTION OF THE INVENTION

I. Compounds of the Invention

As hereinbefore mentioned the present invention relates to a compound of the formula I wherein one or two of $R^1$, $R^2$, and $R^3$ are the same or different and represent hydroxyl, halo, amino, or alkoxy, and the others of $R^1$, $R^2$, and $R^3$ represent hydroxyl or hydrogen, and one of $R^4$, $R^5$, and $R^6$ represents alkyl, or aryl, and the other of $R^4$, $R^5$, and $R^6$ represents hydrogen.

As used herein the term "alkyl" refers to a straight or branched chain hydrocarbon radical containing no unsaturation and having 1 to 4 carbon atoms. Examples of alkyl groups are methyl, ethyl, 1-propyl, 2-propyl, 1-butyl, methylcyclopropyl, methylcyclohexyl, and cyclobutyl. The term "aryl" used herein refers to radicals having the ring structure characteristic of benzene. Examples of aryl groups are benzyl, pNO-benzyl, and p-methoxybenzyl. The term "alkoxy" refers to a substituent which consists of an alkyl or aryl linked through an ether oxygen having its free valence bond from the ether oxygen. Examples of alkoxy groups are O-methyl, O-allyl, O-propyl, O-benzyl, O-pNO-benzyl and O-p-methyl-benzyl. The term "halogen" refers to a member of the family fluorine, chlorine, bromine, or iodine.

In one embodiment of the invention, compounds of the formula I are provided where $R^6$ is alkyl or aryl, $R^1$ and $R^2$ are hydroxyl, halo, amino or alkoxy, $R^3$ is hydrogen, hydroxyl, alkoxy, halo, and amino, and $R^4$ and $R^5$ are hydrogen. In another embodiment, compounds of the formula I are provided wherein $R^5$ is alkyl or aryl, $R^1$ and $R^2$ are hydroxyl, alkoxy, halo or amino, $R^3$ is hydrogen, hydroxyl, alkoxy, halo, and amino, and $R^4$ and $R^6$ are hydrogen. In yet a further embodiment, compounds of the formula I are provided where $R^4$ is alkyl or aryl, $R^1$ and $R^2$ are hydroxyl, alkoxy, halo or amino; $R^3$ is hydrogen, hydroxyl, alkoxy, halo or amino, and $R^5$ and $R^6$ are hydrogen.

In a preferred embodiment of the invention, compounds of the formula I are provided where one of $R^4$, $R^5$ and $R^6$ are alkyl or aryl and the other of $R^4$, $R^5$ and $R^6$ are hydrogen, $R^1$ and $R^2$ are hydroxyl, and $R^3$ is hydrogen or hydroxyl.

These deoxy forms of the compound of the formula I do not substantially inhibit lysosomal mannosidase activity which is an undesirable side effect of swainsonine.

Particularly preferred compounds of the formula I of the invention are those where: 1) $R^6$ is alkyl or aryl, $R^2$ and $R^3$ are hydroxyl, $R^4$ and $R^5$ are hydrogen and $R^1$ is hydroxyl, alkoxy, halo or amino; 2) $R^6$ is alkyl or aryl, $R^1$ and $R^3$ are hydroxyl, $R^4$ and $R^5$ are hydrogen and $R^2$ is hydroxyl, alkoxy, halo or amino; 3) $R^6$ is alkyl or aryl, $R^1$ and $R^2$ are hydroxyl, $R^4$ and $R^5$ are hydrogen and $R^3$ is hydroxyl, alkoxy, halo or amino; 4) $R^5$ is alkyl or aryl, $R^2$ and $R^3$ are hydroxyl, $R^4$ and $R^6$ are hydrogen and $R^1$ is hydroxyl, alkoxy, halo or amino; 5) $R^5$ is alkyl or aryl, $R^1$ and $R^3$ are hydroxyl, $R^4$ and $R^6$ are hydrogen and $R^2$ is hydroxyl, alkoxy, halo or amino; 6) $R^5$ is alkyl or aryl, $R^1$ and $R^2$ are hydroxyl, $R^4$ and $R^6$ are hydrogen and $R^3$ is hydroxyl, alkoxy, halo or amino; 7) $R^4$ is alkyl or aryl, $R^2$ and $R^3$ are hydroxyl, $R^5$ and $R^6$ are hydrogen and $R^1$ is hydroxyl, alkoxy, halo or amino; 8) $R^4$ is alkyl or aryl, $R^1$ and $R^3$ are hydroxyl, $R^5$ and $R^6$ are hydrogen and $R^2$ is hydroxyl, alkoxy, halo or amino; 9) $R^4$ is alkyl or aryl, $R^1$ and $R^2$ are hydroxyl, $R^5$ and $R^6$ are hydrogen and $R^3$ is hydroxyl, alkoxy, halo or amino; 10) $R^6$ is alkyl or aryl, $R^2$ is hydroxyl, $R^3$, $R^4$ and $R^5$ are hydrogen and $R^1$ is hydroxyl, alkoxy, halo or amino; 11) $R^6$ is alkyl or aryl, $R^1$ is hydroxyl, $R^3$, $R^4$ and $R^5$ are hydrogen and $R^2$ is hydroxyl, alkoxy, halo or amino; 12) $R^5$ is alkyl or aryl, $R^2$ is hydroxyl, $R^3$, $R^4$ and $R^6$ are hydrogen and $R^1$ is hydroxyl, alkoxy, halo or amino; 13) $R^5$ is alkyl or aryl, $R^1$ is hydroxyl, $R^3$, $R^4$ and $R^6$ are hydrogen and $R^2$ is hydroxyl, alkoxy, halo or amino; 14) $R^4$ is alkyl or aryl, $R^2$ is hydroxyl, $R^3$, $R^5$ and $R^6$ are hydrogen and $R^1$ is hydroxyl, alkoxy, halo or amino; 15) $R^4$ is alkyl or aryl, $R^1$ is hydroxyl, $R^3$, $R^5$ and $R^6$ are hydrogen and $R^2$ is hydroxyl, alkoxy, halo or amino.

The present invention contemplates all optical isomers and racemic forms thereof of the compounds of the invention and the formulas of the compounds shown herein are intended to encompass all possible optical isomers of the compounds so depicted. The present invention also contemplates salts and esters of the compounds of the formula I of the invention.

II. Processes for Preparing Compounds

As hereinbefore mentioned, the present invention also provides a process for the preparation of a compound of the formula I as defined herein comprising

(a) when a compound of the formula I is required wherein $R^6$ is alkyl or aryl, reacting a compound of the formula II wherein $R^{1'}$, $R^{2'}$, and $R^{3'}$ are hydroxyl and $R^{4'}$, $R^{5'}$, and $R^{6'}$ are hydrogen, which is blocked at $R^{1'}$ and $R^{2'}$, with appropriate oxidizing and Grignard reagents, deblocking $R^{1'}$ and $R^{2'}$, to produce a compound of the formula I wherein $R^6$ is alkyl or aryl, $R^1$, $R^2$, and $R^3$ are hydroxyl, and $R^4$ and $R^5$ are hydrogen; or, optionally, blocking $R^{3'}$, deblocking $R^{1'}$, and replacing the free hydroxyl at $R^{1'}$ by alkoxy, halo, or amino, and deblocking $R^{2'}$ and $R^{3'}$ to produce a compound of the formula I, wherein $R^6$ is alkyl or aryl, $R^1$ is alkoxy, halo, or amino, $R^2$ and $R^3$ are hydroxyl, and $R^4$ and $R^5$ are hydrogen; or optionally, blocking $R^{3'}$, deblocking $R^{2'}$, replacing the free hydroxyl at $R^{2'}$ by alkoxy, halo, or amino, and deblocking $R^{1'}$ and $R^{3'}$ to produce a compound of the formula I wherein $R^6$ is alkyl or aryl, $R^2$ is alkoxy, halo, or amino, $R^1$ and $R^3$ are hydroxyl, and $R^4$ and $R^5$ are hydrogen; or optionally, deblocking $R^{1'}$, replacing the free hydroxyl at $R^{1'}$ by alkoxy, halo, or amino, and deblocking $R^{3'}$ to produce a compound of the formula I wherein $R^6$ is alkyl or aryl, $R^1$ and $R^2$ are the same or different and are alkoxy, halo, or amino, $R^3$ is hydroxyl, $R^4$ and $R^5$ are hydrogen;

(b) when a compound of the formula I is required wherein $R^5$ is alkyl or aryl, reacting a compound of the formula II wherein $R^{1'}$, $R^{2'}$, and $R^{3'}$ are hydroxyl and $R^{4'}$, $R^{5'}$, and $R^{6'}$ are hydrogen, which is blocked at $R^{1'}$ and $R^{3'}$, with appropriate oxidizing and Grignard reagents, deblocking $R_1'$ and $R^{3'}$, to produce a compound of the formula I wherein $R^5$ is alkyl or aryl, $R^1$, $R^2$, and $R^3$ are hydroxyl, and $R^4$ and $R^6$ are hydrogen; or, optionally, blocking $R^{2'}$, deblocking $R^{1'}$, replacing the free hydroxyl at $R^{1'}$ by alkoxy, halo, or amino, and deblocking $R^{2'}$ and $R^{3'}$, to produce a compound of the formula I wherein $R^5$ is alkyl or aryl, $R^1$ is alkoxy, halo, or amino, $R^2$ and $R^3$ are hydroxyl, $R^4$ and $R^6$ are hydrogen; or, optionally, blocking $R^{2'}$, deblocking $R^{3'}$, replacing the free hydroxyl at $R^{3'}$ by alkoxy, halo, or amino, and deblocking $R^{1'}$ and $R^{2'}$, to produce a compound of the formula I wherein $R^5$ is alkyl or aryl, $R^3$ is alkoxy, halo, or amino, $R^1$ and $R^2$ are hydroxyl, $R^4$ and $R^6$ are hydrogen; or, optionally, deblocking $R^{1'}$, replacing the free hydroxyl at $R^{1'}$ by alkoxy, halo, or amino, deblocking $R^{2'}$ to produce a compound of the formula I wherein $R^5$ is alkyl or aryl, $R^1$ and $R^3$ are the same or different and are alkoxy, halo, or amino, $R^2$ is hydroxyl, and $R^4$ and $R^6$ are hydrogen; or (c) when a compound of the formula I is required wherein $R^4$ is alkyl or aryl, reacting a compound of the formula II wherein $R^{1'}$, $R^{2'}$, and $R^{3'}$ are hydroxyl and $R^{4'}$, $R^{5'}$, and $R^{6'}$ are hydrogen, which is blocked at $R^{2'}$ and $R^{3'}$, with appropriate oxidizing and Grignard reagents, deblocking $R^{2'}$ and $R^{3'}$ to produce a compound of the formula I wherein $R^4$ is alkyl or aryl, $R^1$, $R^2$, and $R^3$ are hydroxyl, and $R^5$ and $R^6$ are hydrogen; or, optionally, blocking $R^{1'}$, deblocking $R^{2'}$, replacing the free hydroxyl at $R^{2'}$ by alkoxy, halo, or amino, and deblocking $R^{1'}$ and $R^{3'}$ to produce a compound of the formula I wherein $R^4$ is alkyl or aryl, $R^2$ is alkoxy, halo, or amino, $R^1$ and $R^3$ are hydroxyl, $R^5$ and $R^6$ are hydrogen; or, optionally, blocking $R^{1'}$, deblocking $R^{3'}$, replacing the free hydroxyl at $R^{3'}$ by alkoxy, halo, or amino, and deblocking $R^{1'}$ and $R^{2'}$, to produce a compound of the formula I wherein $R^4$ is alkyl or aryl, $R^3$ is alkoxy, halo, or amino, $R^1$ and $R^2$ are hydroxyl, and $R^5$ and $R^6$ are hydrogen, or optionally, deblocking $R^{2'}$, replacing the free hydroxyl at $R^{2'}$ by alkoxy, halo, or amino, and deblocking $R^{1'}$, to produce a compound of the formula I wherein $R^4$ is alkyl or aryl, $R^2$ and $R^3$ are the same or different and are alkoxy, halo, or amino, $R^1$ is hydroxyl, $R^5$ and $R^6$ are hydrogen.

The radicals $R^{1'}$, $R^{2'}$ and $R^{3'}$ in the compound of the formula II used in the process of the invention may be blocked using appropriate protective groups. Appropriate blocking and deblocking schemes are known to the skilled artisan (See T. W. Greene, Protective Groups in Organic Synthesis, John Wiley & Sons, New York, 1981). For example, ethers, acetals, ketals, and esters can be used to protect isolated hydroxyl groups. In particular, suitable protective groups which may be used in the process of the invention include O-benzyl, O-p-methoxybenzyl, O-acetoxy, O-haloacetoxy, O-benzoyloxy, and O-allyl. Removal of the protective groups may be carried out using procedures known in the art. For example, a p-methoxybenzyl group may be removed using ceric ammonium nitrate in acetonitrile and water.

Appropriate methods for replacing a free hydroxyl group by alkoxy, halo, or amino in blocked/deblocked compounds of the formula II and various derivatives of compounds of the formula I, are well known to the skilled artisan. In particular, a free hydroxyl group may be converted to an alkoxy group by reacting with alkyl or aryl halide in the presence of a base. To replace the free hydroxyl by a halo group, the compound with the free hydroxyl is first reacted with triflic anhydride, mesyl chloride or tosyl chloride, in the presence of a base like pyridine, to block the hydroxyl with a leaving group such as triflate, mesyl, or tosyl, respectively. The blocked hydroxyl is then replaced by O-benzoate, with inversion, by treatment with sodium benzoate in dimethyl formamide (DMF). The O-benzoate is then de-esterified, blocked again by a suitable leaving group like triflate which, on treatment with tetrabutylammonium halide, is replaced, with inversion, by the respective halide, or on treatment with sodium azide is replace, with inversion, by azido, and subsequently by amino on reduction.

An alkoxy group may be added by dissolving a compound with a free hydroxyl in DMF and adding it to a flask under an inert atmosphere containing a base (e.g. sodium hydride) at low temperature (0° C. to 10° C.). After stirring for a few minutes, benzyl bromide in DMF is added dropwise at low temperature, for example 0° C. to 10° C. The reaction mixture is further stirred at room temperature for 2 to 24 hours. Conventional work-up of the reaction mixture yields the alkoxy (benzyl) compound.

A halo group, for example, fluoro, may be added by dissolving a compound with a free hydroxyl in dichloromethane (DCM) together with a base like pyridine. After cooling at low temperature (−10° C. to −60° C.), an appropriate amount of triflic anhydride, or mesyl chloride, or tosyl chloride is added dropwise. The reaction is allowed to stir at a temperature between 0° C. to 25° C. Conventional work-up of the reaction mixture yields the esterified compound. Treatment of this derivative with sodium benzoate in DMF is carried out immediately, which replaces the leaving group with O-benzoate with inversion. The free hydroxyl is generated by treatment with a base (e.g. sodium methoxide) and then reblocked by a suitable leaving group such as triflate (repeating the above described method). To obtain a fluoro derivative with inversion, the triflate is treated with anhydrous tetraalkylammonium fluorides (preferably tetra n-butyl) or potassium fluoride in a suitable solvent (e.g diethyl ether, tetrahydrofuran or crown ether).

For the introduction of an amino group, the triflate is treated either with sodium azide or benzyl amine in DMF. The product is obtained with an azido or benzyl amine group, with inversion, which on reduction with palladium on carbon in a hydrogen atmosphere gives the free amino group.

In accordance with an embodiment of the invention, compounds of formula I where $R^6$ is alkyl or aryl, $R^1$, $R^2$ and $R^3$ are hydroxyl and $R^4$ and $R^5$ are hydrogen, are prepared from a compound of the formula II in which the hydroxyls at $R^{1'}$ and $R^{2'}$ are appropriately blocked, such as swainsonine acetonide, by oxidation of the free hydroxyl, followed by treatment with the appropriate Grignard reagent and subsequent deblocking.

Compounds of formula I where $R^5$ is alkyl or aryl, $R^1$, $R^2$ and $R^3$ are hydroxyl and $R^4$ and $R^6$ are hydrogen may be prepared from a compound of the formula II in which hydroxyls at $R^{1'}$ and $R^{3'}$ are appropriately blocked, for example with O-benzyl, by oxidation of the free hydroxyl, followed by treatment with the appropriate Grignard reagent and subsequent deblocking. The required compound of formula I with $R^1$ and $R^3$ as O-benzyl, $R^2$ as hydroxyl, $R^4$, $R^5$ and $R^6$ as hydrogen can be prepared from swainsonine acetonide by blocking the free hydroxyl ($R^3$) with benzyl, then removing the acetonide group followed by phase transfer benzylation.

Compounds of formula I where $R^4$ is alkyl or aryl, $R^1$, $R^2$ and $R^3$ are hydroxyl and $R^5$ and $R^6$ are hydrogen can be prepared from a compound of the formula II in which hydroxyls at $R^{2'}$ and $R^{3'}$ are appropriately blocked, such as with $R^{2'}$ and $R^{3'}$ as O-benzyl, by oxidation of the free hydroxyl, followed by treatment with the appropriate Grignard reagent and subsequent deblocking. The required compound of formula I with $R^2$ and $R^3$ as O-benzyl, $R^1$ as hydroxyl, $R^4$, $R^5$ and $R^6$ as hydrogen can be prepared from swainsonine acetonide by blocking the free hydroxyl ($R^{3'}$) with benzyl, removing the acetonide group followed by phase transfer p-methoxybenzylation, conventional benzylation and subsequent removal of the p-methoxybenzyl group.

Compounds of formula I where one of $R^3$ and $R^6$ is alkyl or aryl or hydrogen, and the other is hydrogen, $R^1$ and $R^2$ are hydroxyl and $R^4$ and $R^5$ are hydrogen can be prepared from a compound of the formula II in which hydroxyls $R^{1'}$ and $R^{2'}$ are appropriately blocked, such as swainsonine acetonide, by oxidation of the free hydroxyl, $R^{3'}$, followed by treatment of the resulting 8-oxo or 8-keto compound with the appropriate Wittig reagent (Wittig olefination) and subsequent stereospecific reduction to the alkyl or aryl derivative. Removal of the acetonide by conventional deblocking yields the desired 8-deoxy swainsonine derivative.

Compounds of the formula I where $R^5$ is alkyl or aryl, $R^1$ and $R^2$ are hydroxyl, $R^4$ is hydrogen and one of $R^3$ and $R^6$ is hydrogen, or aryl or alkyl, and the other is hydrogen, can be prepared from a compound of the formula II in which hydroxyl $R^{1'}$ is appropriately blocked and one of hydroxyl $R^{3'}$ and hydrogen $R^{6'}$ have been replaced by hydrogen, or aryl or alkyl and the other is hydrogen, such as 8-deoxy swainsonine with $R^{1'}$ as O-benzyl and one of $R^{3'}$ and $R^{6'}$ as hydrogen, or aryl or alkyl and the other is hydrogen, by oxidation of the free hydroxyl, $R^{2'}$, followed by treatment with the appropriate Grignard reagent and subsequent deblocking. The required compound of formula I with $R^1$ as O-benzyl, $R^2$ as hydroxyl, $R^4$ and $R^5$ as hydrogen, and one of $R^3$ and $R^6$ as hydrogen, or aryl or alkyl and the other is hydrogen, can be prepared from the corresponding 8-deoxy swainsonine derivative prepared as described above with subsequent phase transfer benzylation.

Compounds of formula I where $R^4$ is alkyl or aryl, $R^1$ and $R^2$ are hydroxyl, $R^5$ is hydrogen and one of $R^3$ and $R^6$ are hydrogen, or aryl or alkyl and the other is hydrogen, can be prepared from an 8-deoxy swainsonine derivative in which hydroxyl $R^{2'}$ is appropriately blocked, such as 8-deoxy swainsonine with $R^{2'}$ as O-benzyl and one of $R^{3'}$ and $R^{6'}$ are hydrogen, or aryl or alkyl and the other is hydrogen, by oxidation of the free hydroxyl, $R^{1'}$, followed by treatment with the appropriate Grignard reagent and subsequent deblocking. The required compound of formula I with $R^1$ as hydroxyl, $R^2$ as O-benzyl, $R^4$ and $R^5$ as hydrogen, and one of $R^3$ and $R^6$ as hydrogen, or aryl or alkyl and the other as hydrogen, can be prepared from the corresponding 8-deoxy swainsonine derivative prepared as described above with subsequent blocking of hydroxyl $R^{1'}$ by phase transfer p-methoxybenzylation, then blocking $R^{2'}$ by conventional benzylation with subsequent removal of the p-methoxybenzyl group from hydroxyl $R^{1'}$.

If necessary, the products of the processes described above may be purified by conventional methods such as column chromatography.

Compounds of the formula I with available hydroxyl groups can be converted to epi-isomers by SN2 inversion. For example, the free hydroxyl can be reacted with mesyl chloride and pyridine to give O-mesyl (methyl sulphonyl), which on treatment with sodium benzoate in DMF (dimethyl formamide) produces a compound where the free hydroxyl group is replaced by epi-O-benzoate. Deesterification using NaOMe in methanol results in a compound of the formula I where the free hydroxyl is replaced by epihydroxyl. Similarly, this SN2 inversion method can be used to displace a hydroxyl by an azido group or halo group (F, Cl, I, Br) in their epi-isomers.

The compounds of the formula I described above may be converted into salts by reaction with an alkali metal halide, for example, sodium chloride, sodium iodide or lithium iodide. Preferably, the compounds of the formula I are converted into their salts by reaction with a stoichiometric amount of sodium chloride in the presence of a solvent such as acetone. The conversion to the corresponding salts is generally carried out in the temperature range −20° C. to 80° C. and the reaction times are between about 1 to 12 hours.

Compounds of the formula I with free hydroxyl groups may also be converted into esters using conventional procedures. For example, the compounds of the formula I may be dissolved in DCM and pyridine. After cooling (0° C. to 5° C.) benzoic anhydride or benzoyl chloride in DCM and pyridine is added dropwise. The reaction is allowed to stir at room temperature for 2 to 24 hours. Conventional work-up yields the esterified derivatives.

Optical antipodes of the compounds of the formula I may be prepared from the corresponding racemic forms by standard optical resolution techniques, involving, for example, the separation of diastereomeric salts of those compounds of the formula I characterized by the presence of a basic amino group, and an optically active acid, or by synthesis from optically active precursors.

Figure 1:
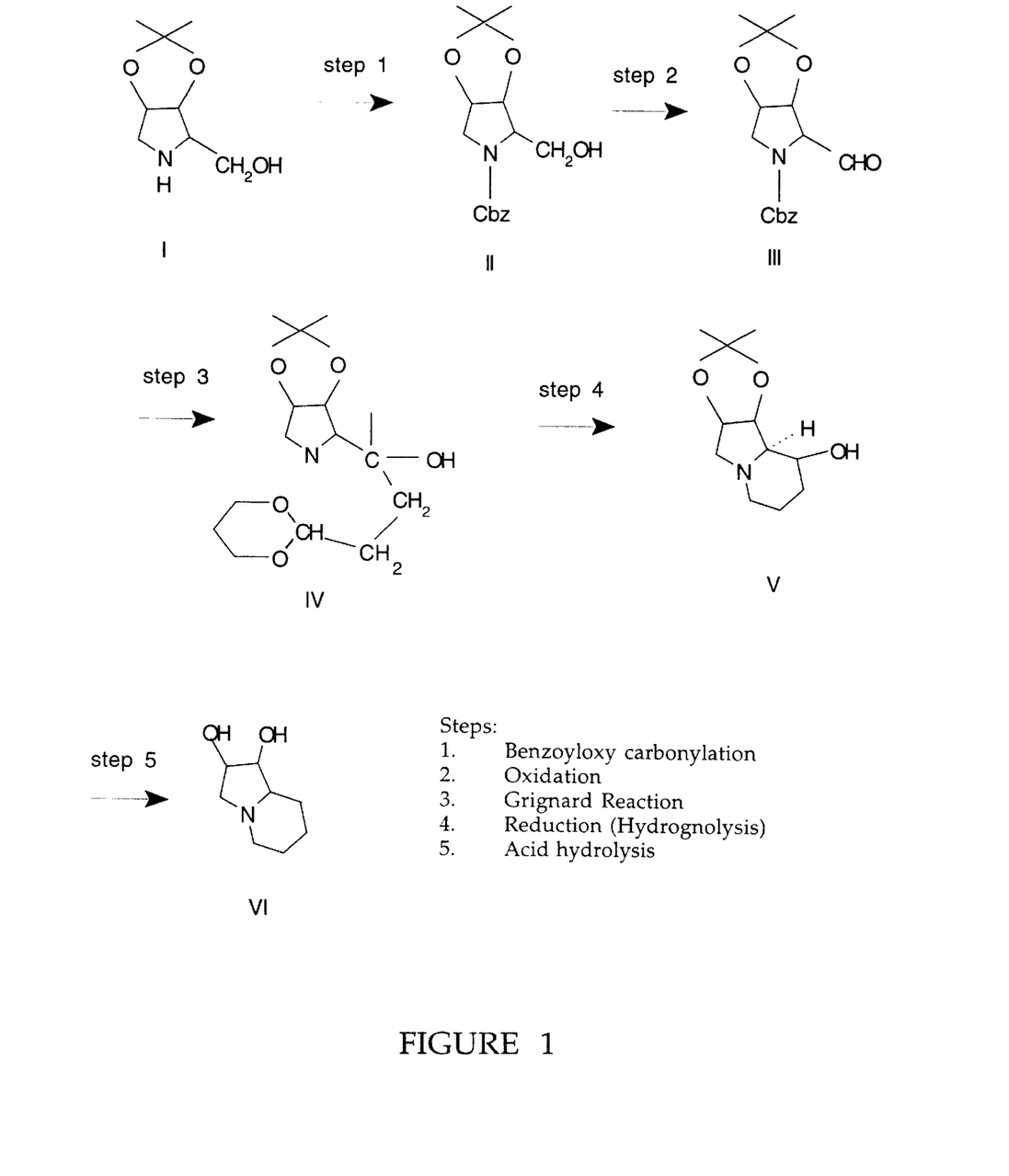
FIGURE 1 is a schematic diagram of a novel reaction for preparing swainsonine.

The invention also provides a novel process for preparing swainsonine which may be used as a starting material in the process of the invention. The reaction scheme is shown in FIG. 1. The process comprises blocking the NH group of O-isopropylidene-1,4-imino-D-lyxitol as N-benzyloxycarbonyl (N-Cbz), oxidizing to give a compound of the formula III, reacting the compound of the formula III with a suitable Grignard reagent to give a compound of the formula IV, and hydrogenolyzing the compound of the formula IV to produce a compound of the formula V, which on acid hydrolysis gives swainsonine.

III. Utlilty of Compounds of the Invention

The compounds of the formula I are inhibitors of oligosaccharide processing and in particular are inhibitors of mannosidase. General mannosidase inhibition may be tested by measuring the inhibition of Jack Bean, α-mannosidase, and lysosomal α-mannosidase. Mannosidase inhibition may also be tested using an L-PHA toxicity assay. The assay is based on the finding that the specific binding of the toxic plant lectin L-PHA to transformed cell lines such as MDAY-D2 tumor cells is a specific measure of inhibition of oligosaccharide processing. The measurement of $IC_{50}$ in the L-PHA toxicity assay reflects the ability of the compound to enter into cells and to effect inhibition of oligosaccharide processing. It is a general screen for activity in cells which measures cell entry, inhibition of the target enzyme, α-mannosidase II in the Golgi, and the resulting cellular phenotype.

Therefore, a compound of the invention may be tested for its ability to inhibit N-linked oligosaccharide processing by growing transformed cells in the presence of L-PHA and the compound; measuring the amount of proliferation of the cells; and determining the ability of the compound to inhibit N-linked oligosaccharide processing by comparing the amount of proliferation of the cells with the amount of proliferation observed for the cells grown in the presence of L-PHA alone.

Transformed cells which may be used in this assay include MDAY-D2, L1210, CHO, B16, melanoma tumor cells, and human tumor cells such as SW 480, LS174T, HT-29, WiDr, T2, MDA-231, MCF7, BT-20, Hs578T, K562, Hs578T, SK-BR-3, CY 6T, MDA-468, H23, H157, H358, H1334, H1155, H28, H460, Hmesol, H187, H510A, N417, H146, H1092, H82 (Restifo, N. P. et al, J. Exper. Med. 177:265–272, 1993).

The amount of proliferation of the cells may be measured using conventional techniques. For example, cell proliferation may be measured by measuring incorporation of labeled thymidine. More particularly, radioactively labeled thymidine may be added for about 2–5 hours, preferably 3–4 hours and the cells can be harvested and radioactivity counted using a scintillation counter.

The conditions for carrying out the above assay will be selected having regard to the nature of the compound and the cells employed. For example, if the transformed cells are MDAY-D2 tumor cells a concentration of about $1-4 \times 10^4$ cells, preferably $2 \times 10^4$ may be used. The MDAY-D2 cells are generally cultured for about 10 to 30 hours, preferably 18 to 20 hours, followed by addition of L-PHA at a concentration of about 10–50 μg/ml preferably 20–30 μ/ml, most preferably 25 μg/ml.

In accordance with a preferred embodiment of the invention, the following L-PHA assay may be used to assay for inhibition of oligosaccharide processing (ie. Golgi α-mannosidase II) in viable cells. MDAY-D2 tumor cells are inoculated into 96 well micro-test plates at $2 \times 10^4$ cells/well, containing serial dilutions of the compound to be tested in MEM plus 10% FCS. The cells are cultured for 18–20 hours, followed by the addition of L-PHA at 25 μg/ml for an additional 24 hours. Cell proliferation is measured by adding 0.5 μCi/well of 3H-thymidine for 3–4 hours, harvesting onto glass fibre disks using a Titertek harvester, and counting the disks in a liquid scintillation counter. The apparent $IC_{50}$ values for the test compounds are the drug concentrations showing 50% protection from L-PHA toxicity; that is 50% 3H-thymidine incorporated compared with cells grown in the absence of L-PHA.

The ability of the compounds of the formulae I in which the free hydroxyls have been esterified, to be converted into more active compounds in cells can be measured by performing the L-PHA toxicity assay in the presence of an esterase inhibitor such as diethyl p-nitrophenyl phosphate. In accordance with a preferred embodiment, the esterase inhibitor diethyl p-nitrophenyl phosphate can be added to MDAY-D2 cells in the above described preferred assay method about 4 hours prior to the α-mannosidase inhibitors. An increase in $IC_{50}$ in the L-PHA toxicity assay in the presence of diethyl p-nitrophenyl phosphate indicates that the compound requires activation by esterases and would accordingly be useful as a prodrug. This method may be used to screen for prodrugs and can be used to identify substances which inhibit all steps in the N-linked oligosaccharide pathway prior to β1+l-4 Gal-transferase.

The compounds of the formula I have valuable pharmacological properties. In particular, the compounds have immunostimulatory, antimicrobial and anti-cancer effects. The anti-cancer effects of the compounds may be demonstrated using a lung colonization assay. For example, melanoma cells treated with a compound may be injected into mice and the ability of the melanoma cells to colonize the lungs of the mice may be examined by counting tumor nodules on the lung after death. Suppression of tumor growth in mice by the compound administered orally or intravenously may be examined by measuring tumor volume.

The compounds of the formula I may be used to stimulate bone marrow cell proliferation. The myeloproliferative activity of a compound of the formula I or II may be determined by injecting the compound into mice, sacrificing the mice, removing bone marrow cells and measuring the ability of the compound to stimulate bone marrow proliferation by directly counting bone marrow cells and by measuring clonogenic progenitor cells in methylcellulose assays.

As immunostimulatory substances the compounds of the formula I may be used in cases where the patient has been immunocompromised such as patients infected with HIV and other viruses or infectious agents, in patients undergoing bone marrow transplants, and in patients having various cancers. The compounds also have an antiviral effect in particular on membrane enveloped viruses such as retroviruses, influenza viruses, cytomegaloviruses and herpes viruses. The compounds are also useful in the prevention, treatment and prophylaxis of metastasis of tumors.

The compounds may be especially useful in the treatment of various forms of neoplasia such as leukemias, lymphomas, melanomas, adenomas, sarcomas, and carcinomas of solid tissues. In particular the composition may be useful for treating malignant melanoma, pancreatic cancer, cervico-uterine cancer, cancer of the kidney, stomach, lung, rectum, breast, bowel, gastric, liver, thyroid, neck, cervix, salivary gland, leg, tongue, lip, bile duct, pelvis, mediastinum, urethra, bronchogenic, bladder, esophagus and colon, and Kaposi's Sarcoma which is a form of cancer associated with HIV-infected patients with Acquired Immune Deficiency Syndrome (AIDS). The compounds may also be used for other antiproliferative conditions such as arthrosclerosis and viral infections, in particular AIDS.

The compounds may be converted using customary methods into pharmaceutical compositions. The pharmaceutical compositions contain the compounds either alone or together with other active substances. Such pharmaceutical compositions can be for oral, topical, rectal, parenteral, local, inhalant, or intracerebral use. They are therefore in solid or semisolid form, for example pills, tablets, creams, gelatin capsules, capsules, suppositories, soft gelatin capsules, liposomes (See U.S. Pat. No. 5,376,452), gels, membranes, and tubelets. For parenteral and intracerebral uses, those forms for intramuscular or subcutaneous administration can be used, or forms for infusion or intravenous or intracerebral injection can be used, and can therefore be prepared as solutions of the compounds or as powders of the active compounds to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays, for example nose sprays, should be considered.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, the compounds in association with one or more pharmaceutically acceptable vehicles or diluents, and contained in buffered solutions with a suitable pH and iso-osmotic with the physiological fluids.

The compounds are indicated as therapeutic agents either alone or in conjunction with other therapeutic agents or other forms of treatment. For example, the compounds may be used in combination with antitumor agents, antimicrobial agents or antiinflammatories. The compositions and agents of the invention can be intended for administration to humans or animals.

In general, a dosage range of the compounds in the composition is envisaged for administration in human medicine of from about 0.01 to 20 mg/kg of body weight daily. In the case of parenteral compositions of this invention, the dosage is about 0.5 to about 25% by weight of the compounds in solution.

Amounts of drug administered to produce serum levels 10–1000 × the $IC_{50}$ for inhibition of oligosaccharide processing in the L-PHA assay are preferably employed.

It will also be appreciated that it may be necessary to deviate from the amounts mentioned and in particular to do so as a function of the body weight of the animal to be treated, the particular disease to be treated, the nature of the administration route and the therapy desired. In addition, the type of animal and its individual behaviour towards the medicine or the nature of its formulation and the time or interval at which it is administered may also indicate use of amounts different from those mentioned. Thus it may suffice, in some cases, to manage with less than the above-mentioned minimum amounts whilst in other cases the upper limit mentioned must be exceeded. Where major amounts are administered, it may be advisable to divide these into several administrations over the course of the day.

The following examples are offered by way of illustration, and not by way of limitation.

EXAMPLES

Example 1

Swainsonine [(1S,2R,8R,8aR)-1,2,8-trihydroxyoctahydroindolizine]

Swainsonine can be synthesized using N-benzyl 1,4-dideoxy-2,3-di-O-isopropylidene-1,4-imino-D-lyxitol which may be synthesized using art recognized methods such as those described by George W. J. Fleet et al., J. Chem. Soc. Chem. Commun. (1984) 1240–1241. The precursor is oxidised with PCC(pyridiniumchlorochromate) and molecular seives in dichloromethane. The aldehyde derivative is then treated with 2-(2-bromoethyl)-1,3-dioxolane and lithium or magnesium in diethyl ether or tetrahydrofuran (The Barbier Reaction). N-benzyl 1,4-dideoxy-5R-[(2-ethyl)-1,3-dioxolane]-2,3-O-isopropylidene-1,4-imino-D-lyxitol is purified from its other possible 5S isomer. Hydrogenolysis of 3 with Pd\C in acetic acid-methanol mixture produces a 1,2-O-isopropylidene-swainsonine. Treatment of 1,2-O-isopropylidene-swainsonine with aq. CF3COOH removed the acetonide group and gave swainsonine after purification on an ion-exchange column.

Example 2

(−)-(1S,2R,8R,8aR)-1,2-O-isopropylidenedioxy-8-hydroxyindolizidine (swainsonine acetonide) 1

1

(−)-(1S ,2R,8,8aR)-1,2-O-isopropylidenedioxy-8-hydroxyindolizidine (swainsonine acetonide) is synthesized using the methods set out in G. W. J. Fleet M. J. Gough and P. W. Smith Tetrahedron Lett. Vol. 25, No. 17 PP 1853–1856 (1984) and Marilyn J. Schneider, Frank S. Ungemach, Harry P. Broquist and Thomas M. Harris, Tetrahedron Vol. 39, No. 1, pp 29–32 (1983), which are herein incorporated by reference.

Example 3

(−)-(1S,2R,8aR)-1,2-O-isopropylidenedioxy-8-oxo-indolizidine 2

2

(−)-(1S,2R,8aR)-1,2-O-isopropylidenedioxy-8-oxo-indolizidine 2 was synthesized using the following process steps. Oxalyl chloride (0.312 mmol) was added under argon to a round bottom flask containing dichloromethane (12 ml) which was precooled to −60° C. To this content, DMSO (dimethyl sulphoxide) (0.680 mmol) was added dropwise over 5 minutes. Stirring was continued at −60° C. for another 10 minutes followed by slow addition of compound 1 (0.283 mmol) dissolved in dichloromethane (3 ml) over 5 minutes. The reaction mixture was stirred for 15 minutes at the same temperature and TEA (triethyl amine) (1.410 mmol) was added dropwise over 5 minutes. The cooling bath was removed and water (1 ml) was added to the reaction mixture at room temperature. After 10 minutes of stirring, the mixture was extracted with dichloromethane (30 ml). The separated aqueous layer was re-extracted with dichloromethane (20 ml). The organic layers were combined and concentrated to a crude syrup which was purified from salt impurities by passage through a silica column with ethyl acetate: methanol (6:1) as solvent. The purified compound thus obtained was directly consumed for the next step.

Example 4

(−)-(1S,9R,8aR)-1,2O-isopropylidenedioxy-8-hydroxy-8c-methyl-indolizidine 3

3

(−)-(IS.9R.8aR)-1,2-O-isopropylidenedioxy-8-hydroxy8-methyl-indolizidine 3 was synthesized using the following method. Under an argon atmosphere a solution of 8-oxoindolizidine derivative 2 in 3 ml of pre-dried tetrahydrofuran was added dropwise with stirring over a 15 minute period to 5 ml of tetrahydrofuran solution containing the Grignard reagent (0.565 mmol, methyl magnesium bromide 1.4 M solution in toluene:tetrahydrofuran 3:1). The reaction mixture was stirred at room temperature for 1 hour and then subjected to gentle reflux for 3 hours. The stirring was continued for another 24 hours at room temperature. The reaction was quenched by dropwise addition of 2 ml hydrochloric acid (10%) at 4–5° C. The mixture was extracted with 25 ml of ethyl acetate. The extract was washed with saturated aqueous sodium chloride, sodium bicarbonate, dried over sodium sulphate, filtered and evaporated to give a mixture of the title compound and its 8-epi-isomer.

Example 5

(−)-(1S,2R,8aR)-1,2,8-tri-hydroxy-8-C-methyl-indolizidine 4 and its 8-epi-indolizidine 4'

The synthesis of (−)-(1S,2R,8aR)-1,2,8-tri-hydroxy-8-C-methyl-indolizidine and its 8-epi-indolizidine was carried out as follows. A mixture of compound 3 and its 8-epi-indolizidine derivative was stirred in 4 ml of trifluoroacetic acid and water (1:1) solution for 48 hours. The solution was concentrated under reduced pressure and the residue was dissolved in 4 ml of water. This was neutralized with dilute alkaline solution and then vigorously extracted with ethyl acetate three to four times. Separation and evaporation of the extract gave a mixture of deblocked isomers which were purified from organic and inorganic impurities by HPLC.

Example 6

(−)-(1S,2R,8aR)-1,2-O-isopropylidenedioxy-8-C-(R)-isopropyl-indolizidine 5

Under an argon atmosphere a solution of the 8-oxoindolizidine derivative 2 (100 mg, 0.474 mmol) in pre-dried tetrahydrofuran (6 ml) was added dropwise with stirring over 15 minutes to a solution of tetrahydrofuran (10 ml) containing the Grignard reagent (1.4 mmol, isopropyl magnesium chloride, 0.7 ml of 2.0M solution in THF). The reaction mixture was refluxed overnight under anhydrous conditions. After 18 hours of reaction, a solution of NaOH (2 ml, 15%) was added at −5° C. to −10° C. to the reaction mixture which was then diluted with ethyl acetate (50 ml) and the organic layer was washed with water (50 ml). The aqueous layer was then re-extracted with ethyl acetate (50 ml). The combined organic layer was dried over sodium sulphate, filtered, concentrated and purified on a filter with silica gel, packed in hexane and pre-washed with 0.1% triethylamine in hexane. The syrupy mixture was analyzed on GC-MS and purified on HPLC. The analysis confirms the stereospecificity of the synthesis.

$^1$H NMR (CDCl$_3$): δ 4.58 (m, 1H, H-1); 4.56 (m, 1H, H-2); 3.39 (m, 1H, H3a); 2.927 (s, 1H, OH); 2.893 (dddd, 1H, J=10.98, 6.49, 1.77, 1.77, H5e); 2.366 (dd, 1H, J=9.32, 4.94, H3b); 2.248 (d, 1H, J=5.22, H8a); 2.083 (ddd, 1H, J=12.28, 10.78, 3.3, H5a); 2.022 (septet, 1H, J=6.86, CH,iPr); 1.68 (H6a), 1.63 (H7e); 1.58 (H6a); 1.496 (s, 3H, CH$_3$—C—O); 1.316 (s, 3H, CH$_3$—C—O); 1.239 (m, 1H, J=13.28, 4.95, H7a); 0.999 (d, 3H, CH$_3$, iPr.); 0.952 (d, 3H, CH$_3$, iPr.)

Example 7

(−)-(1S,2R,8R,8aR)-1,2-O-isopropylidenedioxy-8-hydroxy-8-C-(S)-isopropyl-indolizidine 6.

Compound 5 can be converted to its 8-O-triflate derivative by reacting with Tf$_2$O in DCM and pyridine at low temperature (0° C. to −6° C.). On treatment with sodium benzoate in DMF should give the 8-O-benzoate derivative with inversion from which the 8-C-(S)-isopropyl isomer 6 could be achieved by de-esterification with sodium methoxide in methanol and purification.

From the foregoing, it will be appreciated that, although specific embodiments of the invention have been described herein for purposes of illustration, various modifications may be made without deviating from the spirit and scope of the invention. Accordingly, the invention is not limited except by the appended claims.

We claim:

1. A compound of the formula I wherein two of $R^1$, $R^2$, and $R^3$ are the same or different and represent hydroxyl, halo, amino, or alkoxy, and the other of $R^1$, $R^2$, and $R^3$ represents hydroxyl or hydrogen, and one of $R^4$, $R^5$, and $R^6$ represents alkyl or aryl and the other of $R^4$, $R^5$, and $R^6$ represents hydrogen, and isomers and salts thereof.

2. A pharmaceutical formulation comprising a compound of the formula I as claimed in claim 1 as an active agent, and a pharmaceutically acceptable carrier, excipient, or diluent.

3. A method for stimulating the immune system, treating proliferative disorders, or microbial infections in an individual comprising administering an effective amount of a compound of the formula I as claimed in claim 1.

4. A method for stimulating bone cell proliferation comprising administering an effective amount of a compound of the formula I as claimed in claim 1.

* * * * *